United States Patent [19]

Pelerin

[11] 4,382,788

[45] May 10, 1983

[54] WORKING WELL

[76] Inventor: Joseph J. Pelerin, 3756 Shallowbrook, Bloomfield Hills, Mich. 48013

[21] Appl. No.: 223,561

[22] Filed: Jan. 8, 1981

Related U.S. Application Data

[63] Continuation-in-part of Ser. No. 115,346, Jan. 25, 1980, Pat. No. 4,353,694.

[51] Int. Cl.³ .............................................. A61C 1/14
[52] U.S. Cl. ...................................... 433/77; 433/102; 422/300
[58] Field of Search ..................... 433/77, 102, 53, 65, 433/72, 74, 75; 206/369, 368, 319, 210, 63.5; 422/300; 128/329 A

[56] References Cited

U.S. PATENT DOCUMENTS

| | | | |
|---|---|---|---|
| 1,553,492 | 9/1925 | Williams | 433/65 |
| 2,666,220 | 1/1954 | Sutch | 422/300 |
| 3,295,208 | 1/1967 | Redtenbacher | 433/77 |
| 3,938,253 | 2/1976 | Barnard et al. | 433/77 |
| 4,182,040 | 1/1980 | Bechtold | 433/77 |
| 4,212,639 | 7/1980 | Schaffner | 433/102 |

*Primary Examiner*—Robert Peshock
*Assistant Examiner*—John J. Wilson
*Attorney, Agent, or Firm*—Gifford, VanOphem, Sheridan & Sprinkle

[57] ABSTRACT

A working well is provided for use during root canal therapy and comprises a base with a closed annular side wall and an elongated stem secured to and extending vertically upwardly from the base. A holder for a plurality of dental implements, such as broaches, is attached to the upper end of the side wall so that the implements depend downwardly from the holder. A slide assembly is vertically slidably mounted to the stem and has a stop member with an abutment surface secured to its lower end. The stop member limits the downward extension of the dental implements from the holder. A locking wheel selectively locks the slide assembly against further vertical movement along the stem.

10 Claims, 4 Drawing Figures

WORKING WELL

CROSS REFERENCE TO RELATED APPLICATIONS

The instant application is a continuation-in-part application of U.S. patent application Ser. No. 115,346, filed on Jan. 25, 1980 and entitled DENTAL KIT FOR PERFORMING ROOT CANALS, now Pat. No. 4,353,694, 10/12/82.

BACKGROUND OF THE INVENTION

I. Field of the Invention

The present invention relates generally to dental instruments and, more particularly, to a working well for use during root canal therapy.

II. Description of the Prior Art

In root canal therapy, the nerve canals of the tooth are removed, sterilized and subsequently filled with inert sealer in order to prevent the future infection of the tooth nerve root. In order to accomplish this, it is essential that the entire root canal, including the root tip, be cleaned and filled to eliminate all organic matter contained within the root canal.

The usual procedure in root canal therapy is to open the tooth into the pulp chamber and then work down to the root end. In order to gain access to the pulp chamber, a hole is drilled through the tooth and subsequently widened by a peeso reamer of Gates Glider. When the tooth hole to the pulp chamber is sufficiently wide, reamers are used to clean out the tooth root.

When the tooth root canal debris is removed, it is important throughout the entire root canal operation that the various implements used to clean out the root do not penetrate beyond the end of the root and irritate the periodontal tissues. The length of the root is initially ascertained by the use of dental x-rays. Once the length of the root is determined, a rubber stopper is placed over each reamer so that the distance between the tip of the reamer and the stopper equals the distance between the top of the tooth and the bottom of the root. Since a plurality of reamers and other implements are used throughout the root canal operation, it has been the previous practice to individually measure and position the stoppers on the various implements used during the root canal therapy. The individual measurement and placement of the stoppers on the reamers is very time consuming and, at times, somewhat inaccurate.

SUMMARY OF THE PRESENT INVENTION

The present invention overcomes the above mentioned disadvantages of root canal therapy by providing a working well to facilitate the rapid and adjustable placement of rubber stoppers on dental implements, such as broaches, reamers and the like.

In brief, the working well of the present invention comprises a base having a bottom wall and a closed annular side wall which is open through its top. The base thus forms a reservoir into which a sterilizing liquid, such as alcohol, is contained. An elongated stem is secured at one end to the base so that the stem extends vertically upwardly through the open top of the base.

A holder is secured to the upper end of the annular side wall. The holder comprises a plate extending over the base and having a plurality of holes formed through it so that dental implements, such as reamers or broaches, can be positioned through the holes. The holes in the holder, however, are smaller in diameter than the rubber stoppers placed over the dental implements. Thus, as a dental implement having a rubber stopper positioned over it is pushed downwardly through a hole in the holder, the rubber stopper abuts against the holder and slides along the implement.

A slide assembly is vertically slidably mounted to the stem and includes a stop member at its lower end with a generally planar and horizontal abutment surface positioned beneath the holes in the holder. An adjustment wheel on the stem varies the vertical position of the slide assembly while a locking wheel locks the slide assembly at any desired adjusted vertical position. A lineal scale is also attached to the stem and provides an indication of the lineal distance between the abutment surface on the stop member and the top surface of the holder.

In operation, the slide assembly is first vertically slidably adjusted by the adjustment knob until the distance between the abutment surface on the stop member and the surface of the holder is equal to the depth of the dental root. The slide assembly is then locked to the stem by the locking member.

A rubber stopper is then positioned over the implement in the conventional fashion. The dental implement is then inserted through a hole in the holder and pushed downwardly until the tip of the instrument abuts against the stop member abutment surface. Since the holder abuts against the rubber stopper, upon the subsequent removal of the implements from the support member, the rubber stopper is positioned the desired distance from the tip of the dental implement. The dental implement is then used in the root canal operation in the normal fashion.

The working well according to the present invention thus provides a device for rapidly and accurately positioning rubber stoppers on dental implements in preparation for a root canal operation.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
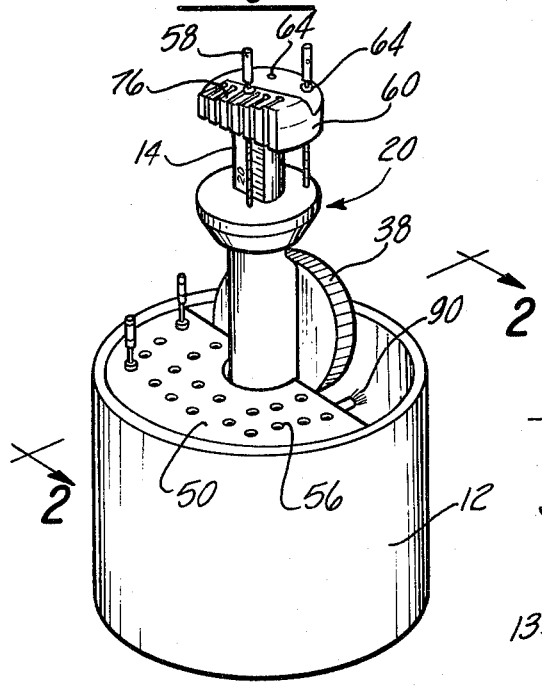
FIG. 1 is a perspective view illustrating a preferred embodiment of the measuring well according to the present invention.
Figure 2:
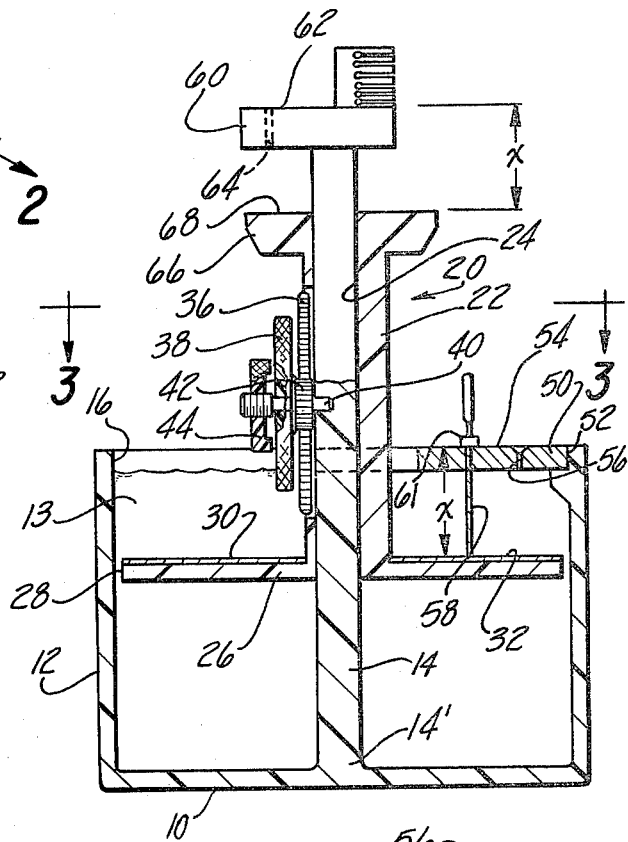
FIG. 2 is a cross sectional view taken substantially along line 2—2 in FIG. 1 and enlarged for clarity.
Figure 3:
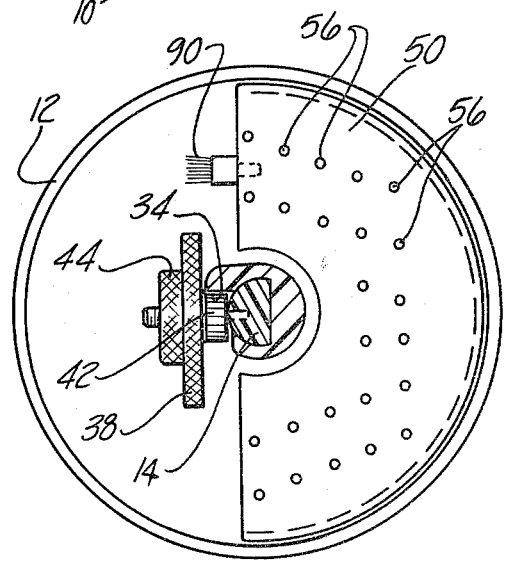
FIG. 3 is a partial sectional view taken substantially along line 3—3 in FIG. 2.

With reference first to FIGS. 1-3 of the drawing, a preferred embodiment of the measuring well according to the present invention is thereshown and comprises a circular base 10 (FIG. 2) having an annular closed side wall 12 extending upwardly from it. An elongated stem 14 having a semicircular cross-sectional shape is attached at its lower end 14' to the center of the base 10 and extends vertically through the open upper end 16 of the side wall 12. In addition, in the preferred form of the invention, the stem 14, base 10 and side wall 12 are of a one-piece construction and constructed of an autoclavable plastic. The base 10 together with the side wall 12 forms a well in which a cold sterile liquid 13 is contained.

With reference now particularly to FIGS. 1 and 2, a slide assembly 20 is vertically slidably mounted on the stem 14. The slide assembly 20 includes a sleeve 22 having a throughbore 24 of the same cross-sectional shape as the stem 14. Thus, the slide assembly 20 can vertically slide along the stem 14 but cannot rotate with respect to the stem 14. A circular stop member 26 is attached to and extends radially outwardly from the lower end of the sleeve 22. The stop member 26, moreover, is dimensioned so that its outer periphery 28 is spaced slightly radially inwardly from the inner periphery of the side wall 12. The top of the stop member 26 is covered by an annular plate 30 which forms an upper abutment surface 32 which faces upwardly through the open end 16 of the side wall 12.

Referring now particularly to FIGS. 2 and 3, a longitudinally extending slot 34 is formed centrally along the slide assembly sleeve 22 and a longitudinally extending gear rack 36 is formed along one side of the slot 34. An adjustment wheel 38 is rotatably mounted to the stem 14 by a shaft 40 and has a gear wheel 42 attached to it which meshes with the gear rack 36. Consequently, rotation of the adjustment wheel 38 longitudinally displaces the slide assembly 20 along the stem 14. A locking wheel 44 is threadably mounted to the shaft 40 coaxially with the adjustment wheel 38. As the locking wheel 44 is tightened, the locking wheel abuts against the adjustment wheel 38 and frictionally locks the adjustment wheel 38 against further rotation which simultaneously locks the slide assembly 20 in its adjusted vertical position.

Referring now to FIGS. 1–3, a semicircular holder 50 is attached at its outer periphery 52 to the upper end of the annular side wall 12 so that the holder 50 is spaced from and parallel to the slide assembly stop member 26. Furthermore, the distance "X" (FIG. 2) between the upper surface 54 of the holder 50 and the upper abutment surface 32 of the stop member 26 decreases as the slide assembly 20 moves upwardly on the stem 14 and vice versa.

A plurality of spaced apertures 56 are formed through the holder 50 so that the apertures are open to and register with the abutment surface 32. These apertures 56 are dimensioned so that a dental implement 58 of the type used in root canal therapy, such as a broach or a reamer, can be positioned through the apertures 56. Furthermore, the apertures 56 are smaller in diameter than a rubber stopper 61 of the type conventionally positioned over the implement.

With reference now to FIGS. 1 and 2, a plate 60 is attached to the upper end of the stem 14 and has an upper planar surface 62. A number of spaced apertures 64, substantially identical in size to the apertures 56, are formed through the plate 60 along its planar surface 62.

An annular member 66 having an upper planar support surface 68 is attached to or formed as a part of the upper end of the slide assembly sleeve 22 so that the planar surface 68 is positioned beneath the openings 64 in the plate 60. Moreover, the slide assembly 20 is longitudinally dimensioned so that the lineal distance between the surfaces 62 and 68 is the same as the lineal distance between the surface 32 on the stop member 26 and the surface 54 on the holder 50. These lineal distances will remain the same despite the vertical position of the slide assembly 20.

Figure 4:
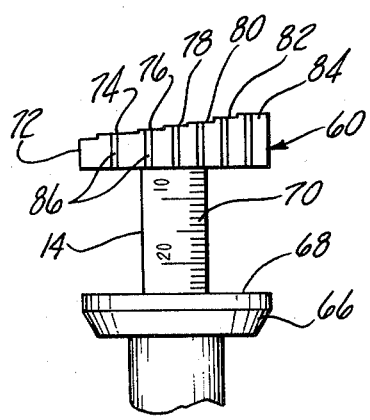
FIG. 4 is a fragmentary side view illustrating a portion of the preferred embodiment of the measuring well of the present invention.

With reference now particularly to FIGS. 1 and 4, an indicia scale 70 on the upper end of the stem 14 provides a visual indication of the lineal distance between the upper surface 62 of the plate member 60 and the surface 68. Simultaneously, of course, the indicia scale 70 provides an indication of the distance between the upper surface 54 of the holder 50 (FIG. 2) and the abutment surface 32 on the stop member 26. In addition, as is best shown in FIG. 4, a stepped plate 72 is formed along one edge of the plate 60. The stepped plate 72 includes a plurality of surfaces 74, 76, 78, 80, 82, and 84 which are vertically offset from each other in predetermined and increasing increments, for example, one half a millimeter. A vertically extending groove 86 is formed along the side of the stepped plate 72 for each surface 74–84. The purpose of the stepped plate 72 will be subsequently described in greater detail.

In operation, the locking wheel 44 is first loosened and the adjustment wheel 38 is then manually rotated which vertically moves the slide assembly 20. The slide assembly 20 is positioned so that the upper surface 68 of the annular member 66 is positioned along the indicia scale 70 a distance the same as the depth of the dental root which must be removed. When the slide assembly 20 is properly positioned in this fashion, the locking wheel 44 is tightened thus holding the slide assembly 20 in its adjusted position.

The rubber stoppers 61 are then placed over the dental implements 58, such as broaches and reamers, and the dental implements are inserted down through the openings 56 in the holder 50 and pushed downwardly to the position shown in FIG. 2. In doing so, the rubber stoppers 61 are all automatically positioned along the dental implements 58 at the same and predetermined distance from the tip of the dental implements 58, and the implement 58 is positioned within the sterile liquid 13. The plurality of holes 56 in the holder 50 enable the rubber stoppers 61 to be placed upon a plurality of different dental implements in preparation for the root canal therapy. The holes 64 in the plate 60 at the top of the stem 14 also provide temporary storage for these dental implements 58.

It is oftentimes necessary, however, to increase the distance between the rubber stoppers 61 and the tip of the dental implement 58 by a small amount, for example, one half millimeter, one millimeter or the like. The stepped plate 72 along one edge of the support member 60 provides a simple, rapid and accurate method for increasing the position of the rubber stopper 61 along the dental implement 58 in small and predetermined increments. For example, if it is desired to increase the distance between the rubber stopper 61 and the free tip of the dental implement 58 by one millimeter, the dental implement 58 is positioned within the groove 86 intersecting the support surface 76 as shown in FIG. 1. The dental implement 58 is then pushed downwardly until its free tip abuts against the surface 68 whereupon the rubber stopper 61 is positioned upwardly along the dental implement 58 by a predetermined amount, in this case, one millimeter. The plurality of different surfaces 74–84 on the stepped plate 72 enables the rubber stopper 61 to be variably positioned along the dental implement 58 in a number of predetermined amounts.

During the root canal therapy, the debris from the tooth root oftentimes clings to the dental implement 58. A small brush 90 (FIGS. 1 and 3) is attached to the support plate 50 to remove this debris from the dental implement 58.

From the foregoing, it can be seen that the measuring well according to the present invention provides a simple, inexpensive and yet highly effective device for rapidly and accurately positioning rubber stoppers on dental implements for use during root canal therapy. The infinitely variable adjustability of the slide assembly 20 along the stem 14 enables the rubber stoppers 61 to be positioned along the dental implements 58 in order to accommodate different patients with different root canal depths.

Having described my invention, however, many modifications thereto will become apparent to those skilled in the art to which it pertains without deviation from the spirit of the invention as defined by the scope of the appended claims.

I claim:

1. A working well for use during root canal therapy comprising:

a base having a side wall, an elongated stem secured at one end to said base so that said stem extends generally vertically upwardly from said base, means for supporting at least one elongated dental implement adjacent the upper end of the side wall so that a portion of the implement depends downwardly from said support means, a slide assembly vertically slidably mounted to said stem and having an abutment surface formed at its lower end and beneath said support means, a plate having an upper surface and at least one aperture formed through it, said plate attached to the upper end of said stem, an annular member secured to the upper end of the slide assembly, said annular member having an upper planar surface positioned beneath said at least one plate aperture, wherein said slide assembly is longitudinally dimensioned so that the lineal distance between said support means and said abutment surface is substantially the same as the lineal distance between at least a portion of the upper surface of said plate and the upper planar surface of said annular member regardless of the position of the slide assembly with respect to the stem, and means for locking said slide assembly to said stem at an adjusted vertical position.

2. The invention as defined in claim 1 and further comprising indicia means on said stem for providing a measurement of said lineal distance between said support means and said abutment member.

3. The invention as defined in claim 1 and further comprising means for vertically slidably moving said slide assembly on said stem.

4. The invention as defined in claim 3 wherein said moving means comprises a gear rack mounted to said slide assembly, a wheel rotatably mounted to said stem and a gear wheel attached to said wheel and in mesh with said gear rack whereby rotation of said wheel vertically displaces said slide assembly.

5. The invention as defined in claim 4 wherein said locking means comprises means for locking said wheel against rotation.

6. The invention as defined in claim 4 wherein said locking means comprises a locking wheel threadably mounted to said stem coaxially with said first mentioned wheel so that upon rotation of said locking wheel in one direction, said locking wheel abuts against and frictionally holds said first mentioned wheel against further rotation.

7. The invention as defined in claim 1 wherein said support means comprises a planar holder attached to the upper end of said side wall, said holder having a plurality of apertures formed through it, each aperture having a diameter less than the diameter of a rubber stopper of the type conventionally positioned over the dental implement.

8. The invention as defined in claim 1 and further comprising a stepped plate secured to said plate for supporting at least two dental implements vertically spaced apart from each other by a predetermined amount.

9. The invention as defined in claim 1 and further comprising a brush secured to said support means.

10. The invention as defined in claim 1 wherein said base and side wall together form a well in which a sterile liquid is contained.

* * * * *